United States Patent [19]

Amemiya et al.

[11] Patent Number: 5,580,441
[45] Date of Patent: Dec. 3, 1996

[54] METHOD OF MEASURING ION CONCENTRATION AND APPARATUS THEREFOR

[75] Inventors: Isao Amemiya, Kawasaki; Noriko Sato; Hiroshi Kikuchi, both of Tokyo, all of Japan

[73] Assignee: Kabushiki Kaisha Toshiba, Kawasaki, Japan

[21] Appl. No.: 357,753

[22] Filed: Dec. 16, 1994

[30] Foreign Application Priority Data

| Dec. 16, 1993 | [JP] | Japan | 5-316602 |
| Mar. 14, 1994 | [JP] | Japan | 6-042576 |
| Mar. 14, 1994 | [JP] | Japan | 6-042714 |
| Mar. 15, 1994 | [JP] | Japan | 6-043763 |

[51] Int. Cl.$^6$ .......................... G01N 33/20; G01N 27/26; G01N 27/333
[52] U.S. Cl. .................. 205/789; 205/781.5; 205/789.5; 205/780.5; 204/416; 204/415; 204/418; 204/409; 204/412; 204/411; 436/73; 436/74; 436/79; 436/110; 436/149; 436/150; 422/82.01; 422/82.02; 422/82.03
[58] Field of Search .......................... 204/153.1, 153.14, 204/153.15, 409, 411, 412, 413, 415, 416, 417, 418, 435; 422/81–82, 82.01, 82.03; 436/74, 73, 79, 110, 149, 150, 151; 205/781.5, 780.5, 789, 789.5

[56] References Cited

U.S. PATENT DOCUMENTS

| 4,627,893 | 12/1986 | Cormier et al. | 204/153.1 |
| 5,004,583 | 4/1991 | Guruswamy et al. | 422/82.03 X |
| 5,098,545 | 3/1992 | Patko | 204/403 |
| 5,288,388 | 2/1994 | Fombon | 204/416 |
| 5,312,986 | 5/1994 | Wilhelm et al. | |

FOREIGN PATENT DOCUMENTS

| 0157597 | 10/1985 | European Pat. Off. | |
| 3823433 | 3/1989 | Germany | |
| 56-155850 | 12/1981 | Japan | 422/82.03 |
| 61-120959 | 6/1986 | Japan | |
| 1244356 | 9/1989 | Japan | |
| 3-180750 | 8/1991 | Japan | 422/82.03 |
| WO92/22811 | 12/1992 | WIPO | |

OTHER PUBLICATIONS

C. Macca et al, *Anal. Chim. Acta* 1983, 154, 51–60.
M. Otto et al. *Anal. Chem.* 1985, 57, 1511–1517.
J. Alonso et al. *Anal. Chim. Acta.* 1986, 179, 503–508.
K. Beebe et al. *Anal. Chem.* 1988, 60, 66–71.
R. J. Forster et al. *Anal. Chem.* 1991, 63, 876–882.

(List continued on next page.)

*Primary Examiner*—Arlen Soderquist
*Attorney, Agent, or Firm*—Oblon, Spivak, McClelland, Maier & Neustadt, P.C.

[57] ABSTRACT

An ion concentration measuring apparatus for measuring the concentration of a measuring ion in a sample solution containing the measuring ion and an interfering ion having the same ionic charge number as that of the measuring ion. This apparatus comprises a first ion-selective electrode for generating a potential in response to the measuring ion, and a second ion-selective electrode in response to the interfering ion. The first ion-selective electrode is brought about in contact with a first, second and third standard solutions, each containing known concentrations of ions. A selectivity coefficient of the ion-selective electrode is calculated on the basis of the output potential of the first ion-selective electrode. The first and second ion-selective electrodes are brought about in contact with the sample solution. The concentration of the measuring ion in the sample solution is calculated on the basis of the output potential of the first and second ion-selective electrodes which have been obtained through the contact thereof with the sample solution and the selectivity coefficient. A ratio between the concentration of the measuring ion and the interfering ion in the first standard solution being identical to a ratio between the concentration of the measuring ion and the interfering ion in the second standard solution, and not identical to a ratio between the concentration of the measuring ion and the interfering ion in the third standard solution.

19 Claims, 8 Drawing Sheets

OTHER PUBLICATIONS

R. J. Forster et al. Anal. Chem. 1992, 64, 1721–1728.
Y. Itoh et al. *Chem. Abstr.* 1992, 116, 98324U.
P. Zhao et al. *Anal. Chem. Acta.* 1992, 258, 27–31.
Patent Abstracts of Japan, vol. 13, No. 580 (P–980), Dec. 21, 1989, JP-A-01 244 356, Sep. 28, 1989.
Biomedizinische Technik, vol. 36, No. 11, pp. 271–284, Nov. 1991, J. G. Schindler, et al., "Ionenselktiver Elektroanalysator Mit Tubularen Festkontakt–Durchflusssensoren Fur Die Kontinuierlich Bioeletrochemisch Kontrollierte Hamodialyse Von K+, Na+,Ca2+, Cl–und pH".
Database WPI, Derwent Publications, AN 85–139790, SU-A 1 124 214, Nov. 15, 1984.
Journal of Neuroscience Methods, vol. 38, No. 2–3, pp. 233–237, Jul. 1991, A. Salt, et al., "Calibration of Ion–Selective Microelectrodes For Use With High Levels of Interfering Ions".

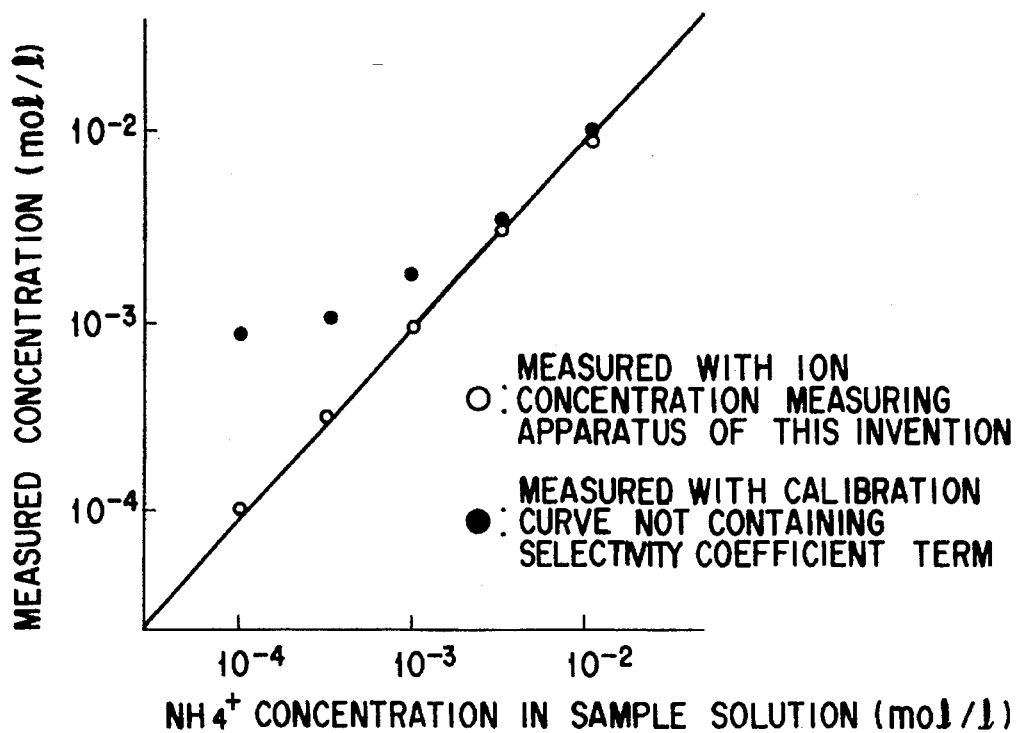
F I G. 8
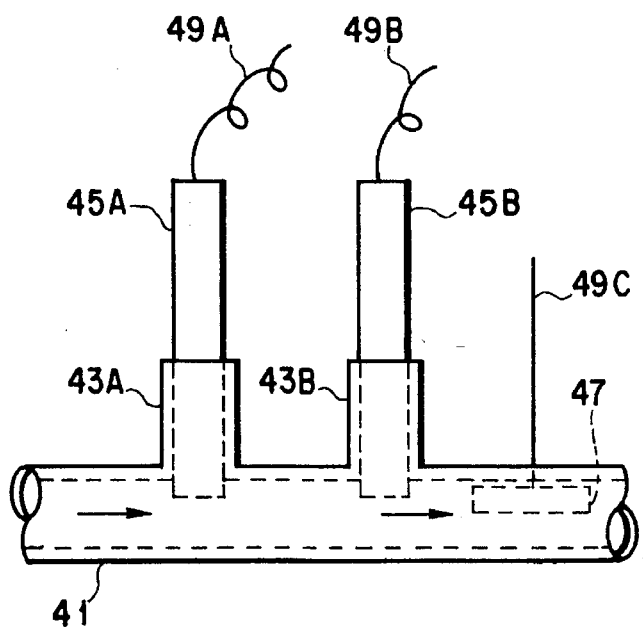
F I G. 9

METHOD OF MEASURING ION CONCENTRATION AND APPARATUS THEREFOR

BACKGROUND OF THE INVENTION

1. Field of the Invention

This invention relates to a method of measuring ion concentration in a nutrient solution, blood or other various solution, and an ion concentration measuring apparatus for carrying out the method. More specifically, this invention relates to improvements in a method of measuring ion concentration, which is capable of eliminating the interference of ions other than an ion to be measured (hereinafter referred to as a measuring ion), and to an ion concentration measuring apparatus for carrying out the method.

2. Description of the Related Art

Conventionally, a potentiometric ion sensor such as an ion-selective electrode or an ion-sensitive field effect transistor has been employed for measuring the concentration of a measuring ion in a sample solution. These sensors are adapted to measure the concentration of an measuring ion in a sample solution on the basis of the following Nernst equation (1).

$$E = E° + \alpha \log(a) \quad (1)$$

where E is output potential of the ion sensor in the sample solution, a is the ion activity (concentration) of a measuring ion in the sample solution, $\alpha$ is the slope (sensitivity) and E° is the output potential (constant) in the standard state. Thus, the equation (1) is inherently formulated for the activity, but the activity can be approximated by the concentration of ion. When a measuring ion is a cation, $\alpha$ becomes positive value, and when it is an anion, $\alpha$ or it becomes negative value.

In this case, $\alpha$ and E° are calculated in advance by using two kinds of standard solutions, each having known ion concentration different from each other. The concentration of a measuring ion can be calculated from the output potential of the ion sensor.

However, an ion sensor may often be influenced to some extent by the interfering ion present in the sample solution. This is because the ion sensor is not exclusively sensitive to the measuring ion, showing some sensitivity to the interfering ion. Therefore, the output of the ion sensor thus obtained is the total of the outputs from the measuring ion and from the interfering ion. Namely, even if the concentration of an measuring ion in a sample solution is constant, the output potential of the ion sensor to be obtained may become altered when the concentration of the interfering ion is varied.

Therefore, when the concentration of an measuring ion is calculated by using the Nernst equation (1), the ion concentration thus calculated may be altered by the influence from the interfering ion even when the concentration of the measuring ion is actually constant, thus setting forth a problem of error in the resultant value. For example, a magnesium ion sensor is susceptible to the interference from calcium ion.

In view of solving the above problem, there has been proposed the Nicholsky-Eiseman equation (2) shown as follows, which is a modification of Nernst equation (1).

$$E = E° + \alpha \log[a_M + \Sigma K_{MN}(a_N)^{m/n}] \quad (2)$$

where E° and $\alpha$ are defined in equation (1), $a_M$ is the activity (concentration) of a measuring ion $M^m$, $K_{MN}$ is a selectivity coefficient to an interfering ion $N^n$, $a_N$ is the activity (concentration) of an interfering ion $N^n$, m and n are the charge numbers of measuring ion and interfering ion respectively, and $\Sigma$ represents the sum total of terms of ions which interferes with the measuring ion $M^m$. The Nicholsky-Eiseman equation is inherently formulated for the activity of ion, but it would not set forth any problem even if the activity of ion is approximated by the concentration of ion.

As for the method of experimentally determining the selectivity coefficient $K_{MN}$ as defined by the Nicholsky-Eiseman equation, it can be classified into two categories as prescribed in the provision of Japanese Industrial Standard (JIS K O122), i.e. mixed solution method and separate solution method.

In this mixed solution method, the selectivity coefficient is calculated as follows. Namely, the concentration of measuring ion is varied in a solution containing a constant concentration of an interfering ion together with the measuring ion to obtain a curve of the output potential of the ion-selective electrode. Then, the tangent of a region of the curve indicating a change in the output potential in proportion to the change in the measuring ion concentration is determined without being influenced by the interfering ion, and at the same time the tangent of a region of the curve indicating no change of the output potential due to the influence from the interfering ion is determined.

Thereafter, the junction of these tangents is determined, and at the same time the concentration of the measuring ion corresponding to the junction is determined. Finally, the selectivity coefficient is calculated from the relationship between the above concentration of the measuring ion and the concentration of the interfering ion. In contrast to the above, there is a method wherein the concentration of interfering ion is varied in a solution containing a constant concentration of a measuring ion together with the interfering ion.

Meanwhile, in the separate solution method, the response characteristic of the output potential is measured in a measuring ion solution as well as in an interfering ion solution respectively, and the selectivity coefficient is calculated either from the concentrations of these ions indicating the same output potential to each other, or from the output potentials of these solutions indicating the same ion concentrations to each other.

According to these methods, theoretically speaking, the determination of the selectivity coefficient can be made on the basis of three output potentials. However, it is required to make use of additional output potentials other than these three output potentials for determining whether or not these three output potentials are of proper locations in the whole potential response curves. Therefore, in the actual experiment for measuring the selectivity coefficient, at least 5 of 6 kinds of standard solutions are required to be used.

For example, in the case of the mixed solution method, it is required as shown in FIG. 1 to measure two output potentials at the points (G) and (I) in order to determine a potential response curve located on an high ion concentration side and showing an output potential which is proportional to the concentration of an measuring ion. It is also required to measure output potential at the location H for determining whether or not these two points are influenced by an interfering ion.

On the other hand, when a potential response curve which is made constant due to the influence from an interfering ion and located on a low ion concentration side is to be determined, it is required to obtain at least two output potentials (A) and (B) for determining whether or not the potential is saturated. Namely, at least five kinds of solutions each having a different ion concentration from one another are required for accurately measuring the selectivity coefficient by means of the mixed solution method.

Moreover, when it is difficult to predict a specific range for the selectivity coefficient, it is also difficult to predict the range of ion concentration centration which indicates a region of change in output potential, so that many measuring points have to be set at small intervals in a wide range of ion concentration, i.e., at least five kinds of standard solutions differing in ion concentration from one another are required in the actual operation.

On the other hand, in the case of the separate solution method, a total of at least 4 kinds of standard solutions differing in ion concentration from one another, i.e., at least two kinds each for obtaining respective potential response curves for the solution of measuring ion and for the solution of interfering ion. However, even with these methods, there are problems that the response curve measured for an interfering ion solution fails to indicate the same potential slope as that of the response curve measured of measuring ion solution, and that the proportional relationship between the output potential and the concentration of ion on the lower concentration side may be lost, thereby setting forth a possibility that precise selectivity coefficient may not be obtained.

Accordingly, in order to carry out precise measurement by using this conventional method, it is required to prepare at least three kinds of solutions for each ion, i.e., a total of 6 kinds of solutions, and at the same time to perform the comparison of potentials at the same ion concentration, or the comparison of ion concentrations at the same potential in the respective linear region of the potential response curve obtained in advance.

As explained above, when the conventional mixed solution method and separate solution method are to be employed for determining the selectivity coefficient of ion-selective electrode against an interfering ion, at least five kinds of solutions are required, and moreover when it is difficult to predict a specific range for the selectivity coefficient, many more kinds of solutions are required, thereby making the measuring operation as well as the calculation involved therefor rather troublesome and complicated.

SUMMARY OF THE INVENTION

The object of the present invention is to provide an ion concentration measuring apparatus which is capable of easily and accurately measuring the concentration of an ion in a solution.

Another object of the present invention is to provide a method of easily and accurately measuring the concentration of an ion in a solution.

A further object of the present invention is to provide a flow-cell type ion concentration measuring apparatus comprising a plurality of ion-selective electrodes, wherein the accuracy of measurement to be obtained by using one of the ion-selective electrodes would never be lower than that where the ion-selective electrode is used singly.

According to a first aspect of the present invention, there is provided an ion concentration measuring apparatus for measuring the concentration of an measuring ion in a sample solution containing the measuring ion and an interfering ion having the same ionic charge number as that of the measuring ion, which comprises: a first ion-selective electrode for generating an output potential in response to the measuring ion; a second ion-selective electrode for generating an output potential in response to the interfering ion; means for sequentially contacting the first ion-selective electrode with a first standard solution, a second standard solution and a third standard solution, each containing known concentrations of the measuring ion and the interfering ion; a first arithmetic means for calculating a selectivity coefficient of the first ion-selective electrode on the basis of the output potential of the first ion-selective electrode, which has been obtained through the contact thereof with the first, second and third standard solutions; means for contacting the sample solution with the first and second ion-selective electrodes; a second arithmetic means for calculating the concentration of the measuring ion in the sample solution on the basis of the output potentials of the first and second ion selective electrodes which has been obtained through the contact thereof with the sample solution and the selectivity coefficient which has been obtained from the first arithmetic means; and a ratio between the concentration of the measuring ion and the interfering ion in the first standard solution being identical to a ratio between the concentration of the measuring ion and the interfering ion in the second standard solution, and not identical to a ratio between the concentration of the measuring ion and the interfering ion in the third standard solution.

According to a second aspect of the present invention, there is provided a method for measuring a concentration of an measuring ion in a sample solution containing the measuring ion and an interfering ion having the same ionic charge number as that of the measuring ion, which comprises: a step of contacting a first ion-selective electrode for generating an output potential in response to the measuring ion sequentially with a first standard solution, a second standard solution and a third standard solution, each containing known concentrations of the measuring ion and the interfering ion; a first calculating step of calculating a selectivity coefficient of the ion-selective electrode on the basis of the output potential of the first ion-selective electrode, which has been obtained through the contact thereof with the first, second and third standard solutions; a step of contacting the sample solution with the first ion-selective electrode; a step of contacting the sample solution with a second ion-selective electrode for generating an output potential in response to the interfering ion; a second calculating step for calculating the concentration of the measuring ion in the sample solution on the basis of the output potentials of the first and second ion-selective electrodes which have been obtained through the contact thereof with the sample solution and the selectivity coefficient which has been obtained from the first calculating step; and a ratio between the concentration of the measuring ion and the interfering ion in the first standard solution being identical to a ratio between the concentration of the measuring ion and the interfering ion in the second standard solution, and not identical to a ratio between the concentration of the measuring ion and the interfering ion in the third standard solution.

According to a third aspect of the present invention, there is provided a flow-cell type ion concentration measuring apparatus for measuring the concentrations of magnesium ion and calcium ion in a sample solution, which comprises a flow-cell channel for passing the sample solution containing magnesium ion and calcium ion; a magnesium ion-selective electrode disposed in the flow-cell channel for detecting the concentration of magnesium ion; and a calcium ion-selective electrode disposed at the downstream of the magnesium selective electrode in the flow-cell channel for detecting the concentration of calcium ion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 8 is a graph illustrating the relationships between an ammonium ion concentration as measured with the apparatus shown in FIG. 7 and the ammonium ion concentration in a sample solution, and between an ammonium ion concentration as measured without compensating the influence of an interfering ion, potassium ion, and the ammonium ion concentration in a sample solution;

FIG. 9 shows a side view illustrating the principal structure of a flow-cell type ion sensor according to a second embodiment of this invention;

DETAILED DESCRIPTION OF THE PREFERRED EMBODIMENT

First, this invention will be explained with reference to FIG. 3 about the outline of method of measuring the selectivity coefficient to be employed in an ion concentration measuring apparatus according to a first embodiment of this invention.

Figure 1:
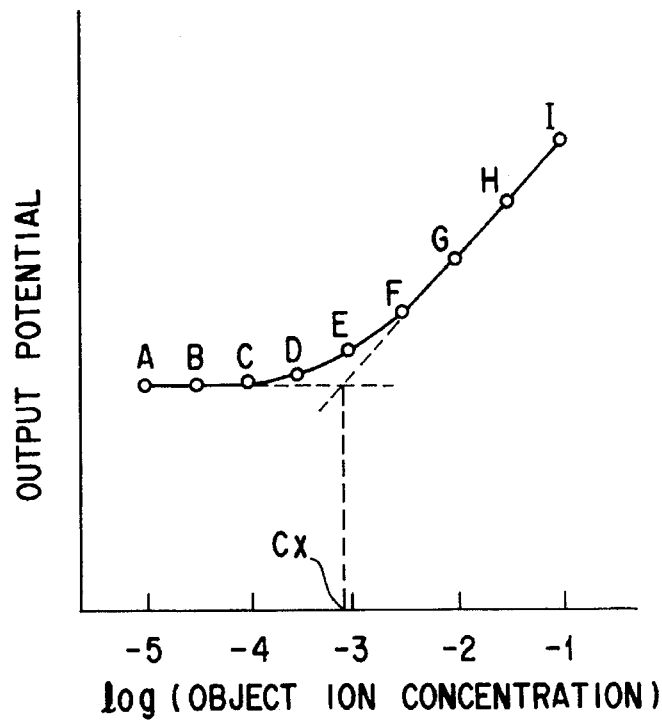
FIG. 1 is a graph illustrating a method of determining a selectivity coefficient according to the conventional mixed solution method.
Figure 2:
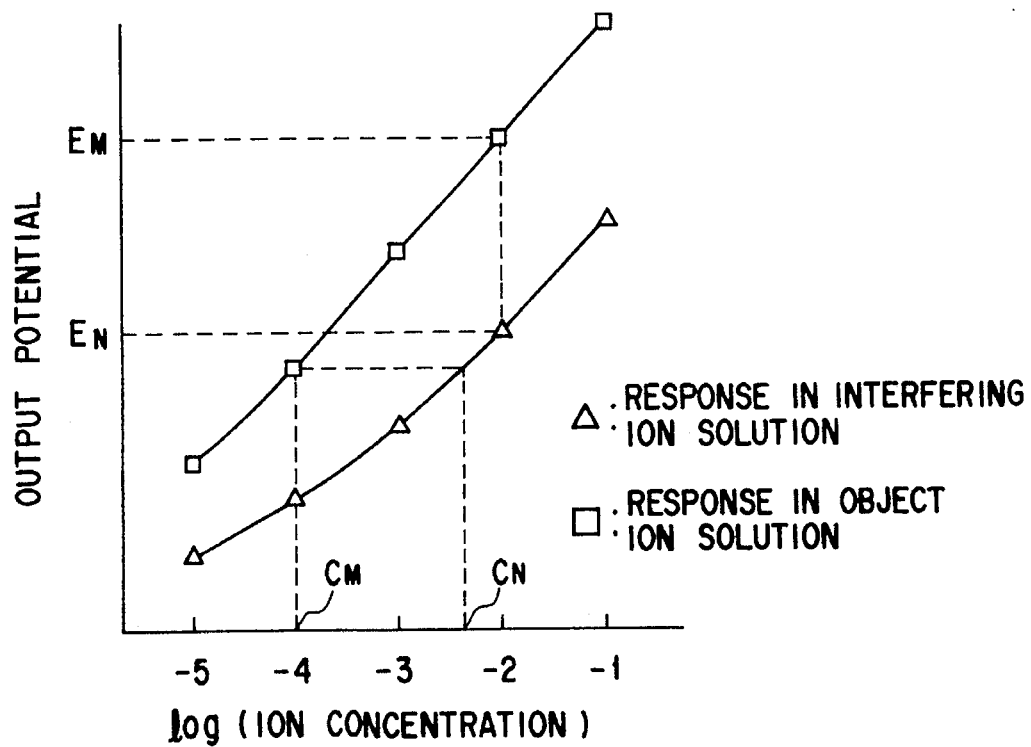
FIG. 2 is a graph illustrating a method of determining a selectivity coefficient according to the conventional separate solution method.
Figure 3:
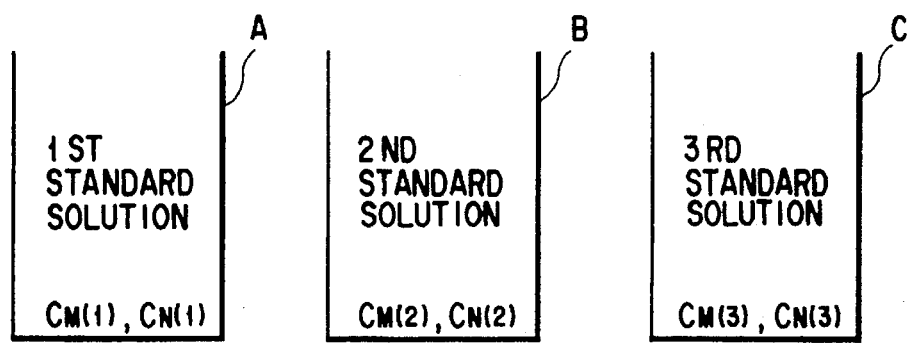
FIG. 3 is a drawing for illustrating the principle which underlies a first embodiment of this invention.

Referring to FIG. 3, in the operation of the ion concentration measuring apparatus according to a first embodiment of this invention, three kinds of standard solutions, each containing known concentrations of the measuring ion $M^z$ (z represents ionic charge number) to be measured by using an ion-selective electrode and the corresponding interfering ion $N^z$ having the same ionic charge number as that of the measuring ion, are prepared. In this case, the concentrations of each of $M^z$ and $N^z$ are adjusted such that the relational expression of $C_{M(1)}/C_{N(1)}=C_{M(2)}/C_{N(2)}\neq C_{M(3)}/C_{N(3)}$ is made valid, where $C_{M(1)}$ and $C_{N(1)}$ represent respectively the concentration of $M^z$ ion and the concentration of $N^z$ ion in a first standard solution, $C_{M(2)}$ and $C_{N(2)}$ represent respectively the concentration of $M^z$ ion and the concentration of $N^z$ ion in a second standard solution, and $C_{M(3)}$ and $C_{N(3)}$ represent respectively the concentration of $M^z$ ion and the concentration of $N^z$ ion in a third standard solution. Then, the ion-selective electrode is rendered to contact with these three kinds of standard solutions to obtain output potentials, and the selectivity coefficient is determined on the basis of these output potentials thus obtained.

In this case, three constants of the following Nicholsky-Eiseman equation (2'), i.e., the selectivity coefficient, the potential slope and standard potential can be determined on the basis of the output potentials of the ion-selective electrode, which have been obtained through the contact thereof with the above three kinds of standard solutions, i.e. the first standard solution A, the second standard solution B and the third standard solution C.

$$E=E°+\alpha\log(a_M+\Sigma K_{MN}\cdot a_N) \qquad (2')$$

wherein $E°$, $\alpha$, $a_M$, $K_{MN}$, and $a_N$ are defined in equation (2).

To be more specific, the concentration of $M^z$ ion can be obtained on the basis of the electrode potential equation (calibration curve), the output potential of the ion-selective electrode to be obtained through the contact thereof with a sample solution containing unknown ion concentration, and the concentration of $N^z$ ion to be obtained through a separate ion-selective electrode for measuring the interfering ion $N^z$. In this case, it is assumed that the ion-selective electrode for measuring $N^z$ ion is not interfered by $M^z$ ion.

It is preferable when performing a more accurate measurement of the selectivity coefficient to adjust the relationship between the $M^z$ ion concentration $C_{M(3)}$ and the $N^z$ ion concentration $C_{N(3)}$ in the third standard solution so as to meet the condition of $C_{M(3)}<C_{N(3)}$.

It is also possible to simultaneously calibrate the ion-selective electrode for measuring $M^z$ ion and the ion-selective electrode for measuring $N^z$ ion, i.e., an interfering ion.

As mentioned above, it is possible according to the ion concentration measuring apparatus of the first embodiment of this invention to determine the selectivity coefficient by using these three kinds of standard solutions wherein the ratio between the concentration of the measuring ion to be measured by the ion-selective electrode and the interfering ion having the same ionic charge number as that of the measuring ion in the first standard solution is made identical to the ratio between the concentration of the measuring ion to be measured by the ion-selective electrode and the interfering ion having the same ionic charge number as that of the measuring ion in the second standard solution, and made different from a ratio between the concentration of the measuring ion to be measured by the ion-selective electrode and the interfering ion having the same ionic charge number as that of the measuring ion in the third standard solution.

Namely, it has become possible according to this invention to easily and accurately measure the selectivity coefficient to an interfering ion having the same ionic charge number as that of the measuring ion by using only three kinds of standard solutions. Moreover, even if it is difficult to predict the range of the selectivity coefficient, it is possible to accurately determine the selectivity coefficient by performing only one measuring operation. Additionally, it has become possible to determine the selectivity coefficient only through a calculation without requiring any graphic processing of output characteristic graph as in the case of the conventional mixed solution method, so that it has become possible to automate quite easily the measurement of the selectivity coefficient.

The ion concentration measuring apparatus according to the first embodiment of this invention will be further explained with reference to the block diagram shown in FIG. 4.

Figure 4:
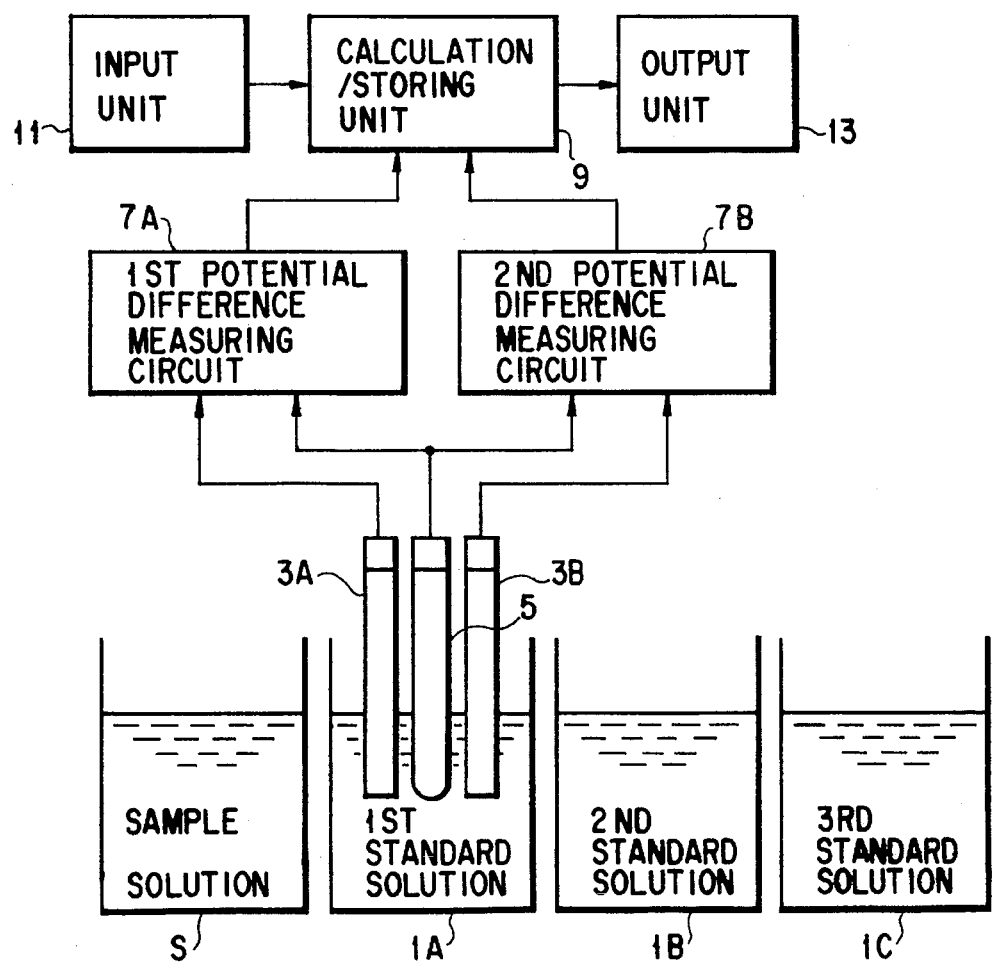
FIG. 4 is a block diagram schematically illustrating the ion concentration measuring apparatus according to the first embodiment of this invention.

Referring to FIG. 4, three kinds of standard solutions, i.e., a first standard solution 1A, a second standard solution 1B and a third standard solution 1C, and a sample solution S are disposed in the ion concentration measuring apparatus of this embodiment, and three kinds of electrodes, i.e., an $M^z$ ion-selective electrode 3A, an $N^z$ ion-selective electrode 3B and a reference electrode 5 are immersed into each of these solutions (for example in the first standard solution as shown in FIG. 4). In this case, it is assumed that the $N^z$ ion-selective electrode 3B is not interfered by $M^z$ ion.

Then, a first potentiometric circuit 7A for measuring the potential difference between the $M^z$ ion-selective electrode 3A and the reference electrode 5 is disposed. Likewise, a second potentiometric circuit 7B for measuring the potential difference between the $N^z$ ion-selective electrode 3B and the reference electrode 5 is disposed. In this case, it is possible to employ a method such that the second potentiometric circuit 7B is omitted, whereby the connection between the first potentiometric circuit 7A and the $M^z$ ion-selective electrode 3A is changed to a connection between the first potentiometric circuit 7A and the $N^z$ ion-selective electrode 3B, and potential differences between the reference electrode 5 and the ion-selective electrodes 3A and 3B are measured. The first potentiometric circuit 7A and the second potentiometric circuit 7B are connected to a calculation and memory element 9 so as to store therein the potential differences measured respectively by the first potentiometric circuit 7A and the second potentiometric circuit 7B. To this calculation and memory element 9 is connected an input element 11 and an output element 13.

The operation of the apparatus shown in FIG. 4 will now be explained below.

The $M^z$ ion-selective electrode 3A to be interfered by $N^z$ ion of the same ionic charge number as that of $M^z$ ion and an $N^z$ ion-selective electrode 3B are immersed together with a reference electrode 5 into each of a first standard solution 1A, a second standard solution 1B and a third standard solution 1C to measure the potential differences (the output potential) between the $M^z$ ion-selective electrode 3A and the reference electrode 5 by means of the first potentiometric circuit 7A, and between the $N^z$ ion-selective electrode 3B and the reference electrode 5 by means of the second potentiometric circuit 7B respectively.

Then, on the basis of the potential differences and the known concentrations of standard solutions fed from an input unit 11, the factor (constant) of the calibration curve for each of the ion-selective electrodes 3A and 3B is determined by the calculation and memory unit 9. Then, these three electrodes 3A, 3B and 5 are immersed into a sample solution S containing unknown concentration of ions in the same manner as mentioned above to measure the potential difference therebetween on the basis of which the concentration of each ion is determined by using the calibration curve prepared in advance.

In this case, the concentrations of each of the $M^z$ and $N^z$ ions are adjusted such that the relational expression of $C_{M(1)}/C_{N(1)}=C_{M(2)}/C_{N(2)}\neq C_{M(3)}/C_{N(3)}$ is made valid (see FIG. 3), where $C_{M(1)}$ and $C_{N(1)}$ represent respectively the concentration of $M^z$ ion and the concentration of $N^z$ ion in a first standard solution, $C_{M(2)}$ and $C_{N(2)}$ represent respectively the concentration of $M^z$ ion and the concentration of $N^z$ ion in a second standard solution, and $C_{M(3)}$ and $C_{N(3)}$ represent respectively the concentration of $M^z$ ion and the concentration of $N^z$ ion in a third standard solution.

When only the selectivity coefficient of the $M^z$ ion-selective electrodes 3A to be interfered by the $N^z$ ion is required to be measured, or when the concentration of the interfering $N^z$ ion in a sample solution is negligibly low, the $N^z$ ion-selective electrode 3B and the second potentiometric circuit 7B may be omitted.

Figure 5:
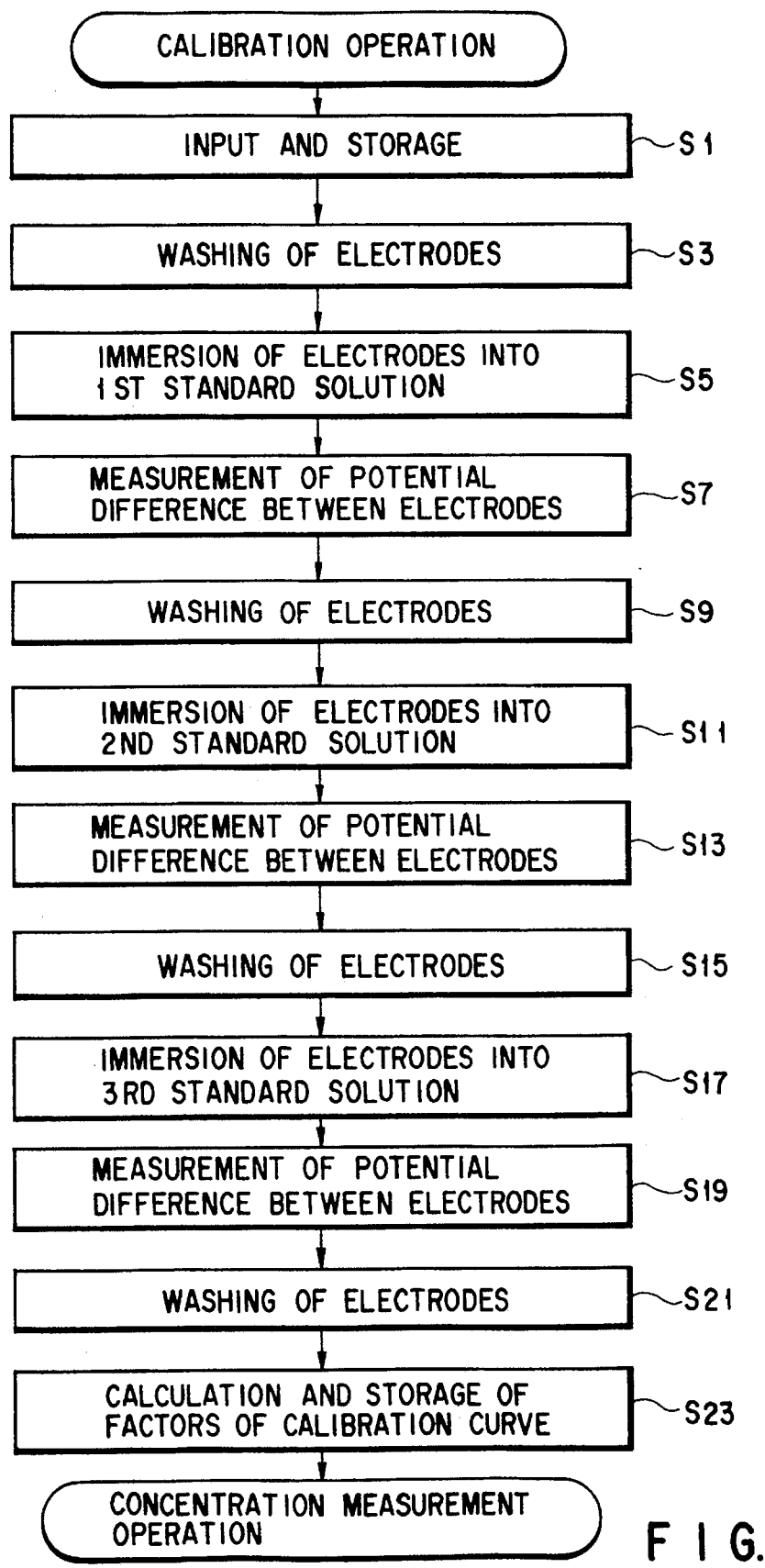
FIG. 5 is a flow chart for illustrating the processes of determining a selectivity coefficient in the ion concentration measuring apparatus shown in FIG. 4.
Figure 6:
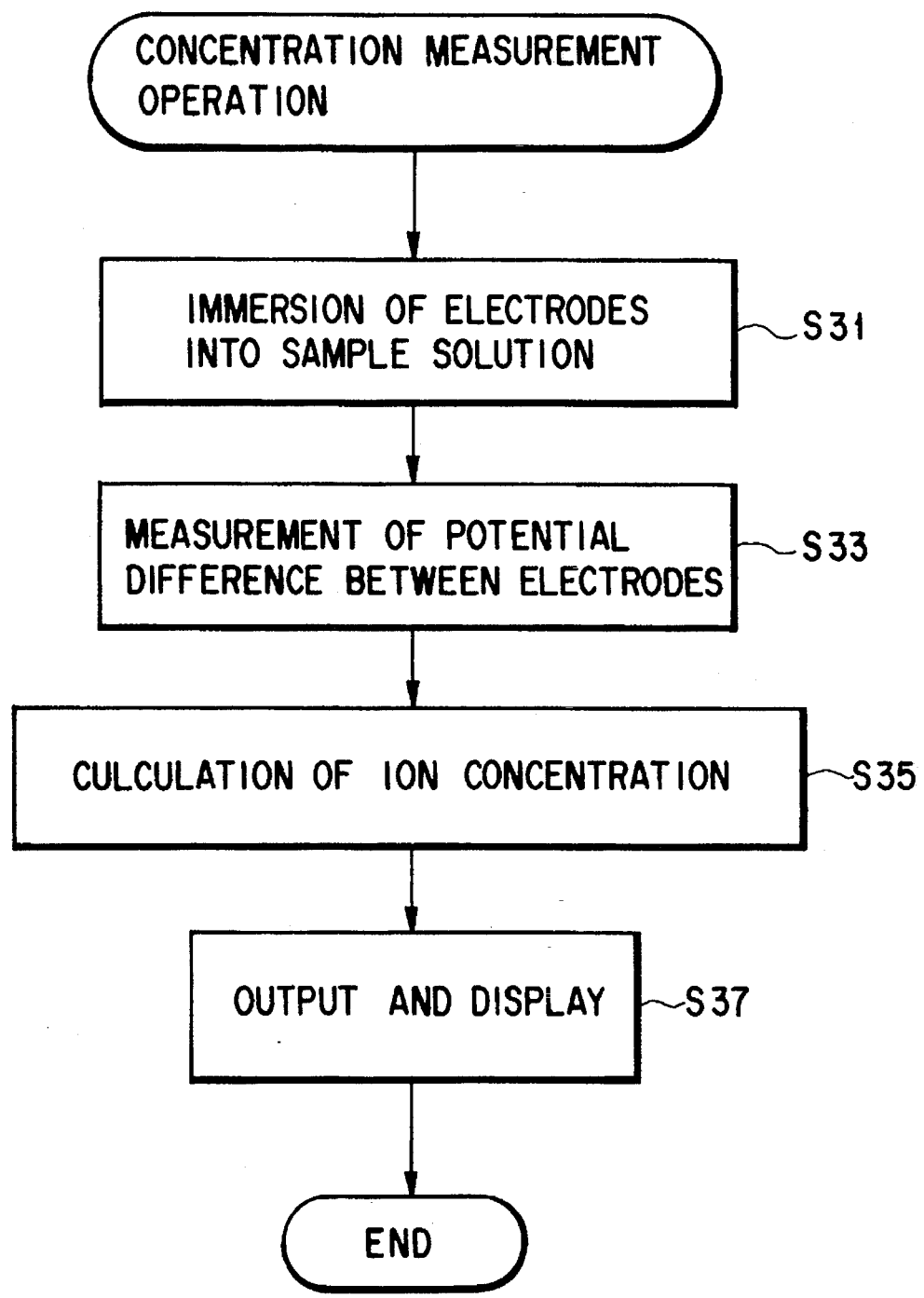
FIG. 6 is a flow chart for illustrating the movement of the ion concentration measuring apparatus shown in FIG. 4.

Now, the operation of the ion concentration measuring apparatus according to this embodiment will be explained with reference to FIGS. 5 and 6. The flow chart shown in FIG. 5 illustrates a calibration operation for determining the factor of the calibration curve for each of the ion-selective electrode, and FIG. 6 shows the operation of measuring ion concentration of a sample solution.

First, the calibration operation will be explained below with reference to FIG. 5. In the step S1, each of the $M^z$ ion concentrations and of the $N^z$ ion concentrations of a first standard solution 1A, a second standard solution 1B and a third standard solution 1C are fed from the input unit 11 and stored into the calculation and memory unit 9.

In the step S3, the washings of the $M^z$ ion-selective electrode 3A, $N^z$ ion-selective electrode 3B and the reference electrode 5 are performed. In the step S5, the $M^z$ ion-selective electrode 3A, $N^z$ ion-selective electrode 3B and the reference electrode 5 thus washed in the step S3 are immersed in the first standard solution 1A. In the step S7, the potential differences between the ion-selective electrode 3A and the reference electrode 5, as well as between the ion-selective electrode 3B and the reference electrode 5, are measured, and the resultant data are stored in the calculation and memory unit 9.

Then, in the step S9, the washings of the $M^z$ ion-selective electrode 3A, $N^z$ ion-selective electrode 3B and the reference electrode 5 used in the steps S3, S5 and S7 are performed. In the step S11, the $M^z$ ion-selective electrode 3A, $N^z$ ion-selective electrode 3B and the reference electrode 5 thus washed in the step S9 are immersed in the second standard solution 1B. In the step S13, the potential differences between the ion-selective electrode 3A and the reference electrode 5, as well as between the ion-selective electrode 3B and the reference electrode 5 are measured, and the resultant data are stored in the calculation and memory unit 9.

Then, in the step S15, the washings of the $M^z$ ion-selective electrode 3A, $N^z$ ion-selective electrode 3B and the reference electrode 5 used in the steps S9, S11 and S13 are performed. In the step S17, the $M^z$ ion-selective electrode 3A, $N^z$ ion-selective electrode 3B and the reference electrode 5 thus washed in the step S15 are immersed in the third standard solution 1C. In the step S19, the potential differences between the ion-selective electrode 3A and the reference electrode 5, as well as between the ion-selective electrode 3B and the reference electrode 5 are measured, and the resultant data are stored in the calculation and memory unit 9.

Further, in the step S21, the washings of the $M^z$ ion-selective electrode 3A, $N^z$ ion-selective electrode 3B and the reference electrode 5 used in the steps S15, S17 and S19 are performed. Then, in the step S23, the factors of the calibration curve of each of the ion-selective electrodes 3A and 3B are calculated on the basis of the ion concentrations and the potential differences of the first standard solution 1A, and the second standard solution 1B and the third standard solution 1C as measured and stored in the calculation and memory unit 9.

Next, the operation of the ion concentration measurement will be explained with reference to FIG. 6. In step S31, the $M^z$ ion-selective electrode 3A, $N^z$ ion-selective electrode 3B and the reference electrode 5 are immersed in the sample solution S. Then, in the step S33, the potential differences between the ion-selective electrode 3A and the reference electrode 5, as well as between the ion-selective electrode 3B and the reference electrode 5 are measured, and the resultant data are stored in the calculation and memory unit 9. In the step S35, the concentrations of the $M^z$ ion and $N^z$ ion are calculated in the calculation and memory unit 9 on the basis of the factors of the calibration curve of each of the ion-selective electrodes 3A and 3B stored in advance and the potential difference measured in the sample solution S. The concentrations of the $M^z$ ion and $N^z$ ion are then supplied to an output unit 13 to be displayed thereon.

When it is desired to perform a more accurate measurement, the procedures shown in FIGS. 5 and 6 are continuously repeated several times. On the other hand, if it is not required to obtain the data of high accuracy, after the calibration operation shown in FIG. 5 is performed once, the operational procedure shown in the flow chart of FIG. 6 may be repeated several times.

The order of operating the standard solutions in the calibration procedure shown in FIG. 5 is not necessarily limited to that shown in FIG. 5, but any other order may be adapted. The washing operation as mentioned herein is not restricted to the washing with pure water or other liquid other than the standard solution, but a standard solution to be used for subsequent measurement of potential, or a sample solution may also be employed as a washing liquid in the washing operation. Further, the washing operation shown in FIGS. 5 and 6 may be omitted. This washing operation can be performed at any other steps or places.

When it is desired not to measure the concentration of ion in a sample solution, but to measure only the selectivity coefficient of $M^z$ ion-selective electrode 3A, the operation of measuring the ion concentration of a sample solution shown in the flow chart of FIG. 6 may be omitted. Further, all operations concerning the $N^z$ ion-selective electrode 3B in the calibration operation shown in FIG. 5 can be omitted. In such a case, the factor of a calibration curve as determined through the calibration of such as the selectivity coefficient, potential slope or standard potential can be represented as the step 31. The flow charts shown in FIGS. 5 and 6 represent the operation of an immersing type measuring apparatus shown in FIG. 4. However, if the operation of immersing in the steps S5, S11, S17 and S31 is replaced by the operation of switching a solution in a flow passage by means of a change-over valve, it may become equivalent to the measuring operation of the flow-cell type flow measuring apparatus.

Figure 7:
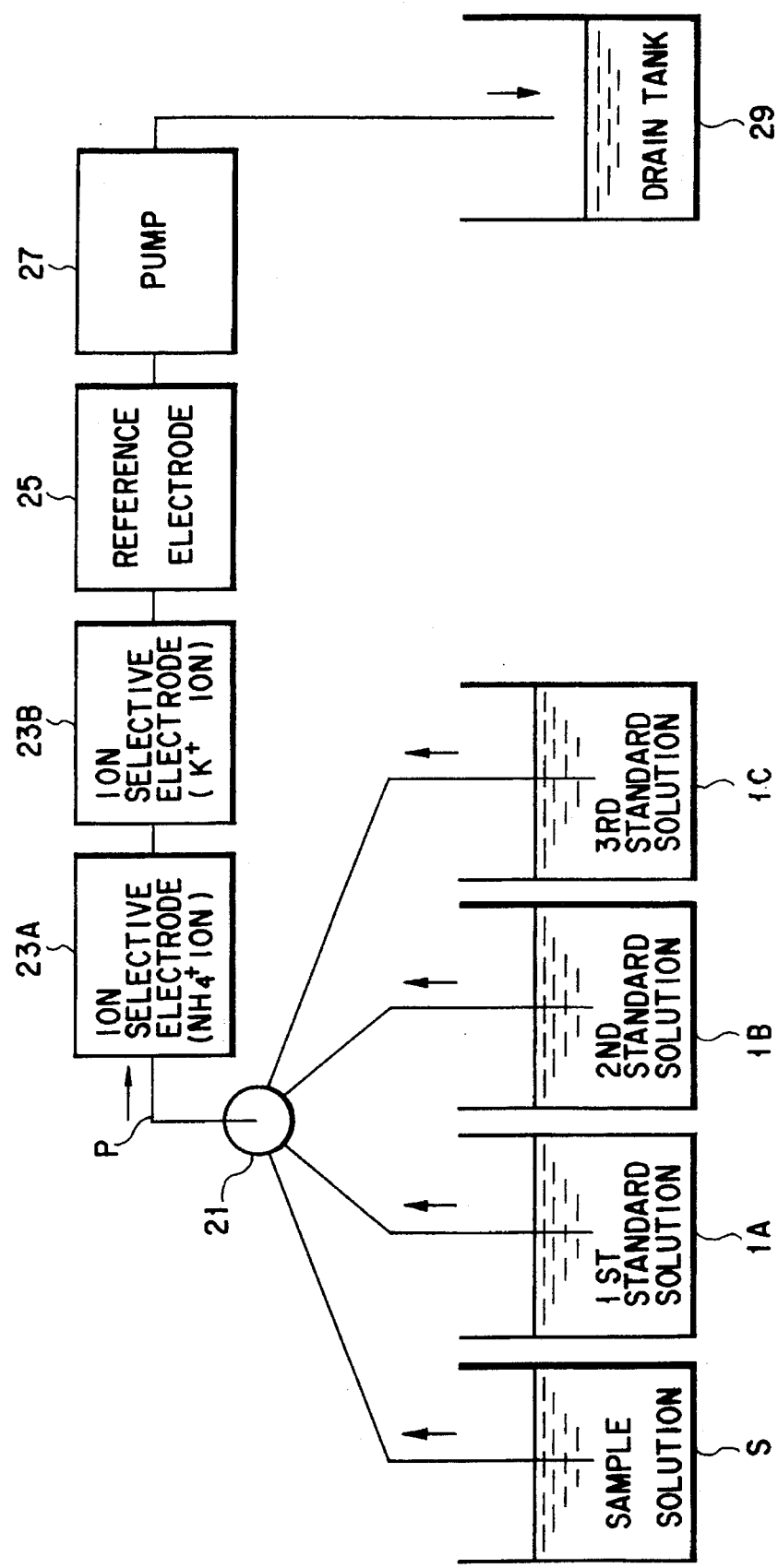
FIG. 7 is a schematic view of a first embodiment of the ion concentration measuring apparatus wherein another solution measuring system is employed.

The measuring system of the ion-selective electrode is not only applicable to the immersing type shown in FIG. 4, but also applicable to the flow-cell type flow measuring system shown in FIG. 7. According to the embodiment shown in FIG. 7, three kinds of standard solutions, i.e. the first standard solution 1A, the second standard solution 1B and the third standard solution 1C as well as the sample solution S are introduced into each of the ion-selective electrodes via a passage P through the operation of a change-over valve 21. These solutions are sucked by a pump 27 disposed at an intermediate portion of the passage, and discharged into a drain tank 29.

The term "ion-selective electrode" referred to in the above embodiment is a general term for indicating a potentiometric ion sensor, and includes an ion sensitive field effect transistor (ISFET).

In the following, a method of measuring selectivity coefficient and a method of measuring ion concentration are explained together with the calculating methods therefor.

When the output potential (potential difference) of the $M^z$ ion-selective electrode 3A to be influenced by the interference from $N^z$ ion is represented respectively by $E_{M(1)}$ with respect to the first standard solution 1A, by $E_{M(2)}$ with respect to the second standard solution 1B and by $E_{M(3)}$ with respect to the third standard solution 1C, the potential slope $\alpha_M$ of the $M^z$ ion-selective electrode 3A, the selectivity coefficient $K_{MN}$ against $N^z$ ion and the standard potential $E_M^\circ$ can be determined respectively by the following equations (3), (4) and (5).

$$\alpha_M = (E_{M(1)} - E_{M(2)})/[\log(C_{M(1)}) - \log(C_{M(2)})] \tag{3}$$

$$K_{MN} = \frac{C_{M(3)} - C_{M(2)} \cdot 10^{(E_{M(3)} - E_{M(2)})/\alpha_M}}{C_{N(3)} - C_{N(2)} \cdot 10^{(E_{M(3)} - E_{M(2)})/\alpha_M}} \tag{4}$$

A calibration curve according to the Nicholsky-Eiseman equation can be formed by using the values of $\alpha_M$, $K_{MN}$ and $E_M^\circ$ determined above.

It is also possible to employ, in place of the above equation (4), the following equation (6), which is equivalent to the equation (4).

$$K_{MN} = -\frac{C_{M(1)} - C_{M(3)} \cdot 10^{(E_{M(1)} - E_{M(3)})/\alpha_M}}{C_{N(1)} - C_{N(3)} \cdot 10^{(E_{M(1)} - E_{M(3)})/\alpha_M}} \tag{6}$$

Meanwhile, a calibration curve of the $N^z$ ion-selective electrode 3B, which is not substantially interfered with by the $M^z$ ion, can be formulated according to the Nernst equation by using the values of the output potential $E_{N(1)}$ and $E_{N(2)}$ derived respectively from the standard solutions 1A and 1B. The potential slope $\alpha_N$ of the $N^z$ ion-selective electrode 3B and the standard potential $E_N^\circ$ can be determined respectively by the following equations (7) and (8).

$$\alpha_n = (E_{N(1)} - E_{N(2)})/[\log(C_{N(1)}) - \log(C_{N(2)})] \tag{7}$$

$$E_N^\circ = E_{N(1)} - \alpha N \cdot \log(C_{N(1)}) \tag{8}$$

When the output potential of the two ion-selective electrodes in the sample solution are represented respectively by $E_{M(S)}$ and $E_{N(S)}$, the $N^z$ ion concentration $C_{N(S)}$ and the $M^z$ ion concentration $C_{M(S)}$ of the sample solution can be determined respectively by the following equations (9) and (10).

$$C_{N(S)} = 10^{(E_{N(S)} - E_N^\circ)/\alpha_M} \tag{9}$$

$$C_{M(S)} = 10^{(E_{M(S)} - E_M^\circ)/\alpha_M} - K_{MN} \cdot C_{N(S)} \tag{10}$$

The calculation result of the above equation (9) can be applied to the value of $C_{N(S)}$ in the equation (10).

In the above ion concentration measuring apparatus, $NH_4^+$ ion-selective electrode containing Nonactin as a sensitive material was used as the ion-selective electrode 3A. This $NH_4^+$ ion-selective electrode is subject to the interference of $K^+$ ion. In this case, three kinds of standard solutions, i.e. a solution of: $C_{NH4(1)}$=5 mmol/l and $C_{K(1)}$=5 mmol/l for the first standard solution 1A, a solution of: $C_{NH4(2)}$=0.5 mmol/l and $C_{K(2)}$=0.5 mmol/l for the second standard solution 1B, and a solution of: $C_{NH4(3)}$=0 mmol/l and $C_{K(3)}$=0.5 mmol/l for the third standard solution 1C were employed, and the selectivity coefficient $K_{NH4,K}$ against $K^+$ ion was measured to obtain the results as shown in Table 1. The values of the selectivity coefficient $K_{NH4,K}$ which were obtained by way of the conventional mixed solution method and the conventional separate solution method are also shown in the Table 1.

TABLE 1

| Method of Measuring Selectivity Coefficient | Number of Solution | Results $K_{NH4,K}$ | Conditions (Concentration of Solution) |
|---|---|---|---|
| Measurement by this invention | 3 | 0.16 | |
| Mixed solution method | 5 | 0.10 | $NH_4Cl$ solution of 0.01 to 100 mmol/l (containing constant concentration of 5 mmol/l KCl) |
| | 9 | 0.15 | |
| Separate solution method | 6 | 0.08 | $NH_4Cl$ solution and, KCl solution of 0.01 to 100 mmol/l (Comparison in concentration at the same potential) |
| | 10 | 0.17 | |

It will be easily understood from the Table 1 that the value of the selectivity coefficient $K_{NH4,K}$ obtained by way of this invention is almost equal to the values of the selectivity coefficient $K_{NH4,K}$ obtained by using 9 or 10 kinds of solutions in the conventional mixed solution method or the conventional separate solution method. On the other hand, the values obtained by using the minimum of 5 or 6 kinds of solutions in the conventional mixed solution method or the conventional separate solution method quite differs from the values obtained by way of measuring methods according to this invention or according to the conventional method using a many number of solutions.

It will be clear from these results that it is possible according to this invention to accurately and promptly determine the selectivity coefficient by using only three kinds of standard solutions. Further, it is not required according to this invention to employ a graphic processing of a graph depicting a potential curve as is required in the conventional methods. Namely, it is possible according to this invention to determine the selectivity coefficient through a simple numerical calculation.

Table 2 shows the results of measurement of the selectivity coefficient wherein the $NH4^+$ ion concentration $C_{NH4(3)}$ and the $K^+$ ion concentration $C_{K(3)}$ in the third standard solution were altered according to this invention. In this case, the ion concentrations of the first standard solution 1A and the second standard solution 1B were: $C_{NH4(1)}$=5 mmol/l and $C_{K(1)}$=5 mmol/l; and $C_{NH4(2)}$=0.5 mmol/l and $C_{K(2)}$=0.5 mmol/l respectively.

TABLE 2

| Ion Concentration of Third Standard Solution | | Selectivity Coefficient (Measured value) $K_{NH4,K}$ |
|---|---|---|
| $NH_4^+$ concentration $C_{NH4(3)}$ (mmol/l) | $K^+$ concentration $C_{K(3)}$ (mmol/l) | |
| 0 | 5 | 0.17 |
| 0.01 | 5 | 0.16 |
| 0.1 | 5 | 0.17 |
| 1 | 5 | 0.22 |
| 6 | 5 | 0.08 |
| 0.1 | 1 | 0.17 |
| 0.05 | 10 | 0.15 |

As clear from the results of the Table 2, when the $C_{K(3)}$ was higher than the $C_{NH4(3)}$, it was possible to obtain more accurate value of the selectivity coefficient.

The $NH_4^+$ ion-selective electrode having its selectivity coefficient $K_{NH4,K}$ against $K^+$ ion determined was employed together with a $K^+$ ion-selective electrode containing valinomycin as a sensitive material to constitute an ion concentration measuring apparatus shown in FIG. 4. The above-mentioned three kinds of standard solutions were employed to calibrate the $NH_4^+$ ion-selective electrode and the $K^+$ ion-selective electrode to formulate calibration expressions as represented by the equations (9) and (10).

Then, these two electrodes were immersed into a sample solution containing unknown concentration of ions, thereby measuring outputs, from which the concentration of each ion was determined by applying them to the calibration curve. The results measured of $NH_4^+$ ion concentration were shown in FIG. 8, wherein the sample solutions employed in the experiment contained a constant amount of 5 mmol/l of KCl and a varied amount of 1 to 10 mmol/l of $NH_4Cl$. The measurement of ion concentration was also conducted by using Nernst equation including no term of the selectivity coefficient as a calibration curve equation for the $NH_4^+$ ion-selective electrode, the results of the measurement being shown also in FIG. 8.

As shown in FIG. 8, the $NH_4^+$ ion concentration as measured by using the selectivity coefficient determined according to this invention was almost the same as the $NH_4^+$ ion concentration of the sample solution, which was compensated of the interference from $K^+$ ion. Namely, the measurement error in this case was within ±9%.

In another experiment, The $Mg^{2+}$ ion-selective electrode containing as a sensitive material N-heptyl-N', N'-bis{8-[[3-(heptylmethylamino)-1,3-dioxypropyl]amino]octyl}-N-methyl-propanediamide, and the $Ca^{2+}$ ion-selective electrode containing as a sensitive material bis[di-(n-octylphenyl)phosphate]calcium were employed to constitute an ion concentration measuring apparatus. This $Mg^{2+}$ ion-selective electrode is subject to the interference from $Ca^{2+}$.

In this case, the $Mg^{2+}$ ion-selective electrode was employed as the ion-selective electrode 3A shown in FIG. 4, and, likewise, the $Ca^{2+}$ ion-selective electrode was employed as the ion-selective electrode 3B shown in FIG. 4. In this case, three kinds of standard solutions, i.e. a solution of: $C_{Mg(1)}$=2 mmol/l and $C_{Ca(1)}$=4 mmol/l for the first standard solution 1A, a solution of: $C_{Mg(2)}$=0.2 mmol/l and $C_{Ca(2)}$=0.4 mmol/l for the second standard solution 1B, and a solution of: $C_{Mg(3)}$=0.1 mmol/l and $C_{Ca(3)}$=4 mmol/l for the third standard solution 1C were employed.

As a result, the selectivity coefficient $K_{Mg,Ca}$ of the $Mg^{2+}$ ion-selective electrode against the $Ca^{2+}$ ion was found to be 0.15. This value of the selectivity coefficient $K_{Mg,Ca}$ was found to be almost the same as the results obtained from the conventional mixed solution method (9 solutions were used) and from the conventional separate solution method (10 solutions were used). Further, it was found preferable as in the case of $NH_4^+$ ion-selective electrode to make the $C_{Ca(3)}$ higher than the $C_{Mg(3)}$ for obtaining more accurate value of the selectivity coefficient.

When $Mg^{2+}$ ion concentration was determined by making use of a calibration curve equation according to the Nicholsky-Eiseman equation having the above obtained value of selectivity coefficient incorporated therein, and of the $Ca^{2+}$ ion concentration obtained from the $Ca^{2+}$ ion-selective electrode, the error in the measurement of 0.1 to 4 mmol/l $MgCl_2$ solution (4 mmol/l $CaCl_2$ being kept constant) was found to be within ±8%.

In still another experiment, The $NO_3^-$ ion-selective electrode containing as a sensitive material trioctylmethylammonium nitrate, and the $Cl^-$ ion-selective electrode containing as a sensitive material silver chloride were employed to constitute an ion concentration measuring apparatus. This $NO_3^-$ ion-selective electrode is subject to the interference from $Cl^-$.

In this case, three kinds of standard solutions, i.e. a solution of: $C_{NO3(1)}$=5 mmol/l and $C_{Cl(1)}$=10 mmol/l for the first standard solution 1A, a solution of: $C_{NO3(2)}$=0.5 mmol/l and $C_{Cl(2)}$=1 mmol/l for the second standard solution 1B, and a solution of: $C_{NO3(3)}$=0.5 mmol/l and $C_{Cl(3)}$=10 mmol/l for the third standard solution 1C were employed to measure the selectivity coefficient $K_{NO3,Cl}$ of the $NO_3^-$ ion-selective electrode against the $Cl^-$ ion, finding a value of 0.07.

When $NO_3^-$ ion was measured by making use of the above obtained value of selectivity coefficient, the error in the measurement of 0.3 to 8 mmol/l $KNO_3$ solution (10 mmol/l KCl being kept constant) was found to be within ±6%.

As explained above, it is possible according to the first embodiment of this invention to accurately and easily determine the selectivity coefficient against an interfering ion having the same ionic charge number as that of an measuring ion by using only three kinds of standard solutions. Further, it is possible to accurately measure a selectivity coefficient by performing only one measuring operation.

Moreover, it is not required according to this invention to employ a graphic processing of a graph depicting an output potential curve as is required in the conventional methods. Namely, it is possible according to this invention to determine the selectivity coefficient through a simple numerical calculation, so that the measuring apparatus can be easily automated. Additionally, it is possible according to this ion concentration measuring apparatus to simultaneously carry out the calibration of another ion-selective electrode for measuring the concentration of an interfering ion by using above-mentioned standard solutions for measuring the selectivity coefficient, and to compensate the influence of the interfering ion to the ion-selective electrode, thereby making it possible to accurately measure the concentration of the measuring ion.

Next, a flow-cell type ion sensor according to a second embodiment of this invention will be explained.

The flow-cell type ion sensor according to a second embodiment of this invention comprises a magnesium ion-selective electrode for detecting the concentration of magnesium ion in a flow passage of a flow cell through which a solution to be measured and containing at least magnesium ion and calcium ion is passed, and a calcium ion-selective electrode disposed downstream of the magnesium ion-selective electrode. Through this arrangement of two sensors, it has become possible to assure the accuracy of the magnesium ion-selective electrode.

The principle for assuring the accuracy of the magnesium ion-selective electrode in the flow-cell type ion sensor according to a second embodiment of this invention will be explained below.

The present inventors have first found and examined the phenomenon of the degradation in measuring accuracy of a magnesium ion-selective electrode such as the PVC (polyvinyl chloride) liquid film type magnesium ion-selective electrode, which will be caused if a plurality of ion-selective electrodes are disposed in a flow-cell type ion sensor. As a result, it has been found that the degradation in measuring accuracy was caused by the lowering of selectivity of the magnesium ion-selective electrode with respect to the calcium ion when the magnesium ion-selective electrode is used together with a calcium ion-selective electrode.

It has been found after examining this phenomenon more in detail that when the measurement of the concentrations of magnesium ion and calcium ion is carried out by disposing both of the magnesium ion-selective electrode and calcium ion-selective electrode in the flow passage of a measuring solution containing at least magnesium ion and calcium ion, the measurement accuracy of the magnesium ion-selective electrode will be lowered as compared with the case where only magnesium ion-selective electrode is employed if magnesium ion-selective electrode is positioned downstream of the calcium ion-selective electrode, and that if magnesium ion-selective electrode is positioned upstream of the calcium ion-selective electrode, the measurement accuracy of the magnesium ion-selective electrode would not be lowered.

In view of above observation, the lowering of the measurement accuracy of the magnesium ion-selective electrode, when it is used together with calcium ion-selective electrode, is deemed to be caused by the interference of components eluted out of liquid film type calcium ion-selective electrode against the magnesium ion-selective electrode. The most probable interfering components are a film solvent contained in a calcium ion-selective electrode, i.e. a substituted phosphonic acid and phosphate, such for example as decan-l-ol, di-n-octylphenyl phosphonate, dioctylphosphonate, tri-n-octylphosphate and tri-n-decylphosphate. It is most probable that these interfering components interfere, via a solution to be measured, with the magnesium ion-selective electrode, and lower the selectivity of the magnesium ion-selective electrode against calcium ion.

There will now be explained a flow-cell type ion sensor according to a first example of the second embodiment of this invention with reference to FIG. 9.

FIG. 9 illustrates a block diagram showing the construction of the flow-cell type ion sensor according to a first example of the second embodiment of this invention. This flow-cell type ion sensor comprises as shown in FIG. 9 a cylindrical flow-cell case 41, to which at least two holders, for example holders 43A and 43B are connected in parallel. Into these holders 43A and 43B are inserted or fitted a magnesium ion-selective electrode 45A and a calcium ion-selective electrode 45B respectively. In this case, the magnesium ion-selective electrode 45A and a calcium ion-selective electrode 45B are inserted in such a manner as to make sure that each tip portion of the electrodes 45A and 45B are capable of being touched by a measuring solution (a solution to be measured) flowing through the flow-cell case 41. This arrangement is also applicable to the case where another ion-selective electrode for detecting another ion is installed therein. In addition to these electrodes 45A and 45B, a reference electrode 47 may also be disposed in the flow-cell case 41 in such a manner that the reference electrode 47 comes in contact with the measuring solution.

To each of the ion-selective electrodes 45A and 45B, and the reference electrode 47 is connected lead wires 49A, 49B and 49C respectively. In this example, the apparatus is arranged such that the measuring solution passes through the flow-cell case 41 from left to right in FIG. 9, so that the magnesium ion-selective electrode 45A is disposed at the upstream side (left side in the drawing), and the calcium ion-selective electrode 45B is disposed at the downstream side of the magnesium ion-selective electrode 45A.

In this example, the reference electrode 47 is disposed at the downstream side of the calcium ion-selective electrode 45B. However, the reference electrode 47 may be disposed between the magnesium ion-selective electrode 45A and the calcium ion-selective electrode 45B, or at the upstream side of the magnesium ion-selective electrode 45A. If another ion-selective electrode is to be mounted on this apparatus, it can be disposed anywhere as in the case of the reference electrode 47 as far as the calcium ion-selective electrode 45B is disposed at the downstream side of the magnesium ion-selective electrode 45A.

Next, the operation of the apparatus of this example will be explained with reference to its specific construction. The ion concentrations of magnesium ion and calcium ion are continuously measured by using the flow-cell type ion sensor according to this example. As mentioned above, a measuring solution containing magnesium ion and calcium ion was passed through the flow-cell case 41 from left to right.

The magnesium ion-selective electrode 45A disposed at the upstream side of the flow passage of the flow cell is composed of a PvC liquid film type electrode wherein N-heptyl-N',N'-bis{8-[[3-(heptylmethylamine)-1,3-dioxypropyl]amino]octyl}-N-methyl-propane diamide was employed as a sensitive material, and o-nitrophenyloctyl ether was employed as a film solvent. On the other hand, the calcium ion-selective electrode 45B disposed at the downstream side of the flow passage of the flow cell is also composed of a PVC liquid film type electrode wherein bis[di-(n-octylphenyl)phosphate]calcium was employed as a sensitive material, and di-n-octylphenyl phosphonate was employed as a film solvent.

A silver-silver chloride electrode was employed as the reference electrode 47. The potential of each of the ion-selective electrodes 45A and 45B was measured using the reference electrode 47 as a base.

When the concentration of magnesium ion contained in each of the measuring solutions each containing varied concentration of calcium ion was measured, the error in any of the measurement was found to be ±7%. Further, it was found that the apparatus can be continuously used for at least four months.

On the other hand, when the positions of the ion-selective electrodes 45A and 45B were interchanged to each other, and the measurement of magnesium ion concentration was conducted under the same conditions as the above-mentioned example, the error in the measurement was ±18%, and at the same time the life of the apparatus was lowered to about one month.

There will be explained a flow-cell type ion sensor according to a second example of the second embodiment of this invention with reference to FIG. 10.

Figure 10:
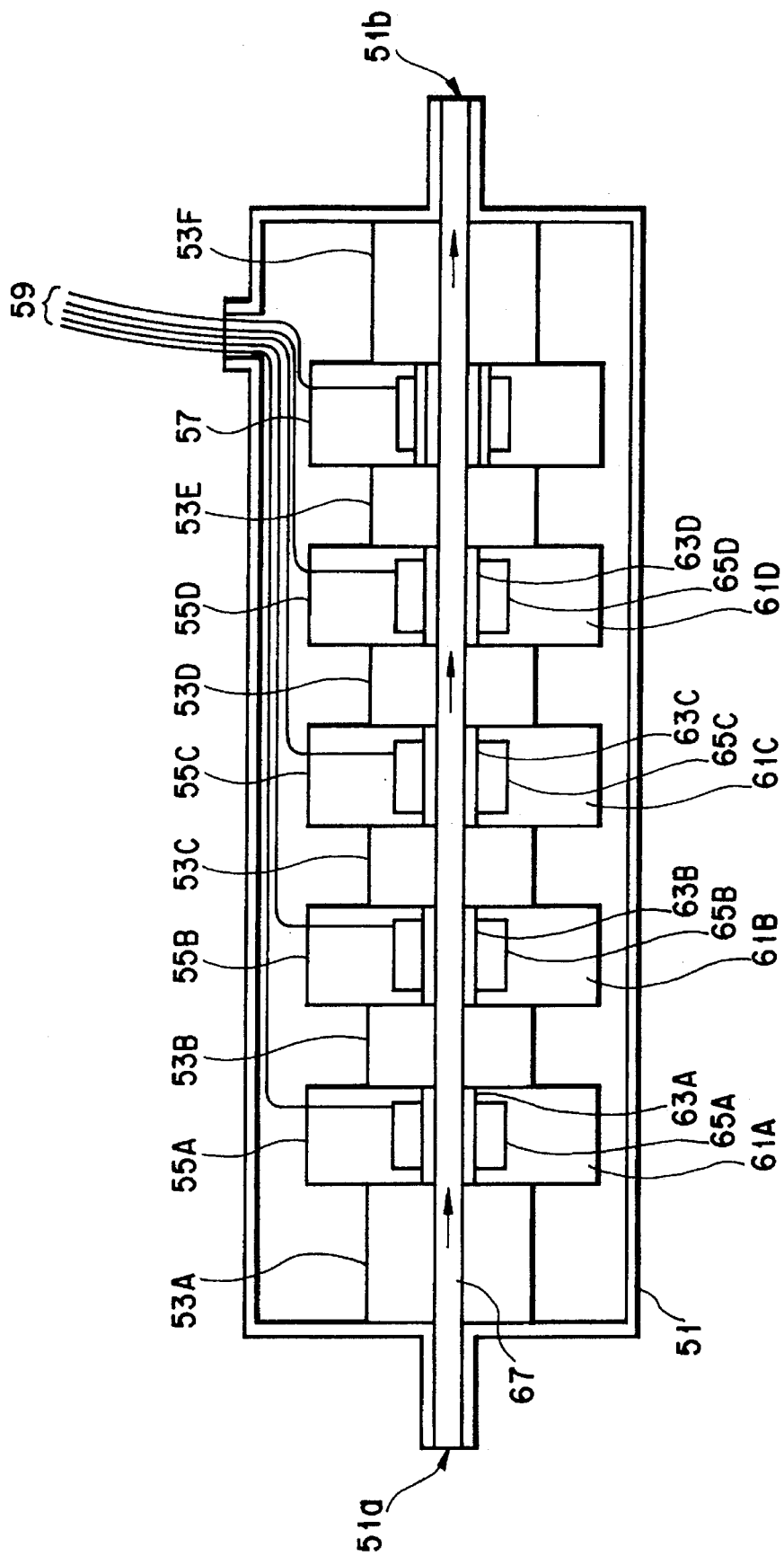
FIG. 10 is a side view illustrating another structure of a flow-cell type ion sensor according to a second embodiment of this invention.

FIG. 10 schematically shows a vertical cross-sectional view of a flow-cell type ion sensor for simultaneously measuring four different kinds of ions. According to this flow-cell type ion sensor, ion-selective electrodes 55A to 55D and a reference electrode 57 are disposed in the outer housing 51. To this outer housing 51 of the ion sensor are attached an inlet port 51a and an outlet port 51b for passing a measuring solution therethrough. Further, an opening for taking out a lead wire 59 is provided on a wall near the outlet port 51b of the outer housing 51.

The magnesium ion-selective electrode 55A, the potassium ion-selective electrode 55B, the calcium ion-selective electrode 55C, the nitrate ion-selective electrode 55D and the reference electrode 57 are formed of almost the same shape to each other, i.e. a disk-like body having the same diameter and provided at the center thereof with a through hole.

Likewise, insulating members 53A, 53B, 53C, 53D, 53E and 53F, each being disposed between the outer housing 51, the ion-selective electrodes 55A, 55B, 55C, 55D and the reference electrode 57, are shaped into the same shape to each other, and provided, as in the case of the ion-selective electrodes 55A to 55D, with a through hole at the center thereof.

There is no specific limitation as to the thickness of any of the insulating members 53B, 53C, 53D and 53E, the insulating member 53A disposed between the inlet port 51a and the ion-selective electrode 55A, and the insulating member 53F disposed between the outlet port 51b and the reference electrode 57, and the thickness of them may be arbitrarily selected.

The above-mentioned ion-selective electrodes 55A, 55B, 55C, 55D, the reference electrode 57, and the insulating members 53A, 53B, 53C, 53D, 53E and 53F are closely and integrally joined face to face in such a manner that their central openings coincide to each other so as to form a through hole 67 therein. Namely, the through hole 67 passing through the insulating members 53A, 53B, 53C, 53D, 53E and 53F, the ion-selective electrodes 55A, 55B, 55C, 55D and the reference electrode 57 functions as a separate passage running between the inlet port 51a and the outlet port 51b for enabling a measuring solution to pass through from the inlet port 51a to the outlet port 51b without causing any leakage of the measuring solution in the way.

Now, the construction of the ion-selective electrode will be explained. Since any of the ion-selective electrodes 55A, 55B, 55C and 55D is almost the same in construction to each other, only the magnesium ion-selective electrode 55A will be explained as an example.

This magnesium ion-selective electrode 55A comprises a base body (preferably, polyvinyl chloride) 61A (61B, 61C, 61D) having a through opening, a magnesium ion-selective film 63A (potassium ion-selective film 63B, calcium ion-selective film 63C, nitrate ion-selective film 63D) is formed along the inner wall of the through opening, a conductive member 65A (65B, 65C, 65D) contacting hermetically with the magnesium ion-selective film 63A, and a lead wire 59 connected to the conductive member 65A. The structure or position of the reference electrode 57 may not be restricted in any manner, but it may be preferable to dispose the reference electrode 57 at the most downstream side of the ion-selective electrodes 55A to 55D.

With this construction, it is possible to form a plurality of ion-selective electrodes into an integrated compact body, and to minimize the flow rate of a measuring solution. Accordingly, the ion sensor according to this invention is excellent in practicability, and suited for an on-line measurement.

The electrode structure according to the second example, which is shown in FIG. 10 can be classified as a so-called coated-wire type ion-selective electrode having no inner liquid. However, this invention is not limited to the electrode structure of this type, and can be applicable to any of electrodes including liquid film type electrodes having an inner liquid.

As explained above, it is possible according to the second embodiment of this invention to improve the measurement accuracy of a magnesium ion-selective electrode in a flow-cell type ion sensor comprising a magnesium ion-selective electrode and a calcium ion-selective electrode as high as that of a sensor wherein a magnesium ion-selective electrode is singly employed.

In the followings, a third embodiment of this invention will be explained with reference to FIGS. 11 to 13B.

Figure 11:
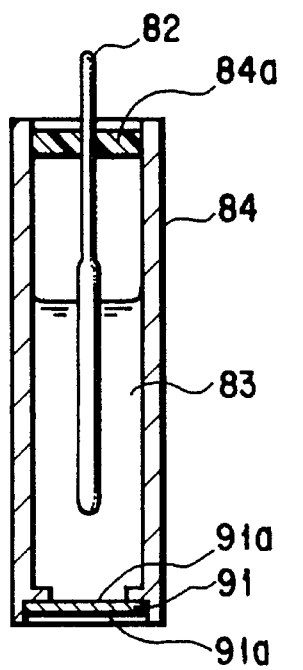
FIG. 11 is a sectional view of the structure of an ion-selective electrode according to a third embodiment of this invention.
Figure 12:
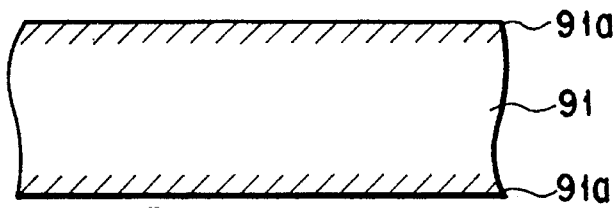
FIG. 12 depicts the ion-sensitive membrane of an ion-selective electrode according to a third embodiment of this invention.

The ion-selective electrode according to the third embodiment of this invention comprises, as shown in FIG. 11, an ion-sensitive membrane 91, an electrode case 84 sustaining the ion-sensitive membrane 91, an inner electrode 82, and an inner liquid 83 to which the ion-sensitive membrane 91 and the inner electrode 82 are contacted. This ion-selective electrode is featured in that the both surfaces 91a of the ion-sensitive membrane 91 are hydrophobic. The reference numeral 84a represents a sealing agent which sustains the inner electrode 82 and at the same time prevents the leakage of the inner liquid. However, the sealing agent may be employed in a manner which is not strictly hermetical.

It has been found through experiments by the present inventors that when the both surfaces of an ion-sensitive membrane are made hydrophobic in an ion sensor for measuring the concentration of ion in a solution, the reproducibility of the potential of an ion-selective electrode can be improved. The ion-sensitive membrane of this kind can be formed by keeping the atmosphere at the moment of evaporating THF solvent from a solution of an ion-sensitive membrane in an inert gas such as nitrogen gas or argon gas and in a low humidity (20% or less, preferably 10% or less in relative humidity) by using a globe box. When the ion-sensitive membrane is formed in this manner, an ion-sensitive membrane having hydrophobic surface on its both surfaces can be obtained.

Figure 13A:
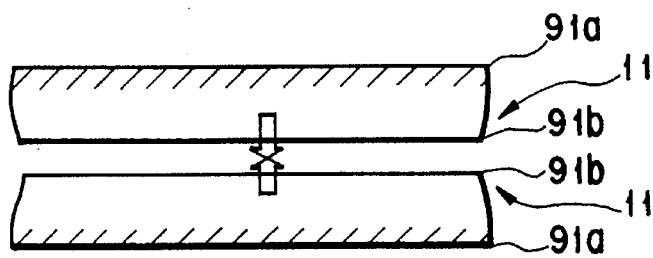
FIGS. 13A and 13B respectively illustrate the manufacturing method of the ion-sensitive membrane of an ion-selective electrode according to a third embodiment of this invention.
Figure 13B:
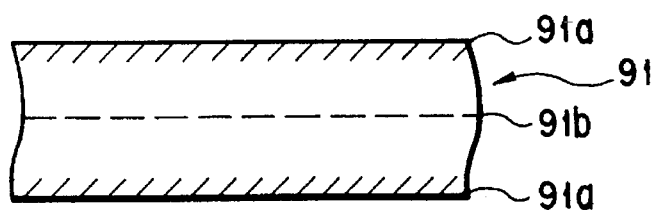

In an alternative method, a couple of films are first formed according to an ordinary method by using a hydrophobic substrate made for example of Teflon (registered trade mark) for spreading a liquid of an ion-sensitive membrane. Then, films thus prepared are adhered together by turning a main surface 91a of each film (a surface which was initially contacted to the substrate and higher in hydrophobic property: the other main surface 91b being lower in hydrophobic property) outside as shown in FIGS. 13A and 13B. In the example shown in FIGS. 13A and 13B, two films of the same thickness are employed for adhering to each other. However, two films to be adhered to each other may be different in thickness from each other, or three of more films may be employed for producing the ion-sensitive membrane. It has been found that in the case of forming a magnesium ion sensitive membrane containing as a sensitive material a compound having (N-methyl-N-heptylmarronamoyl)amino group, an ion-sensitive membrane having a stabilized selectivity against calcium ion can be obtained by adjusting the thickness of the ion-sensitive membrane to be prepared by this method to as thick as 30 µm or more, preferably 50 µm or more.

The process of preparing such an ion-sensitive membrane will be explained by referring to a chloride ion sensor as an example as follows.

As a sensitive material for the chloride ion sensor, methyltridodecylammonium chloride (hereinafter referred to as MTDA-Cl) was employed, and a THF solution of an ion-sensitive membrane was prepared by mixing 25.2% by weight of MTDA-Cl, 33.1% by weight of PVC and 41.7% by weight of DOP (dioctyl phthalate). Meanwhile, two pieces of devices, each comprising a Teflon plate having a smooth polished surface, and a cylindrical glass enclosure having a diameter of 35 mm and fixed to the Teflon plate were prepared. Then, the film solution prepared above was carefully poured into each of the cylindrical glass enclosures so as not to introduce foam into the enclosures. The pouring of the film solution was continued until the height of the film solution in the enclosure reaches to about 3 mm. Subsequently, the THF solvent was caused to evaporate, and after drying the residual film, the resultant film was peeled from the cylindrical enclosure. Then, the peripheral portion having non-uniform thickness was cut off with a punch die, thereby obtaining two films, each having a uniform thickness and a diameter of 20 mm. Then, one of the films was laid down with a main surface (which was initially exposed to outer atmosphere) turned upward, and a little amount of the THF was dripped onto the main surface. Immediately after finishing the dripping of the THF, the other film, with its one main surface initially contacted to the surface of Teflon turned upward, was laid thereover, thereby adhering these two films to each other. In this adhering step, it is important to prevent any foams from interposing between these films. The laminated film thus produced is of completely integrated body in spite of the adhesion of two films, and is essentially equivalent to a separate film having a prescribed thickness which has been prepared from the beginning.

When the contact angles of the both surfaces of the laminated film were measured, it was found to be about 65! on either side. This laminated film differs from the film produced according to the conventional method in that since one main surface of the film produced according to the conventional method was exposed to the outer atmosphere during the manufacturing step thereof, this one main surface differing in characteristic from the other main surface is caused to expose during its use, so that the hydrophobic nature of the film is often deteriorated as a whole even if a hydrophobic plate such as Teflon plate was used as a spreading substrate, whereas in the present invention, the both surfaces of the laminated film are the ones which were contacted to the surface of Teflon during the manufacture thereof, so that surfaces to be exposed during the use are excellent in hydrophobic nature. The adhesion of two film prepared individually can also be carried out by using a THF solution of ion-sensitive membrane itself other than the THF as in the case of this embodiment. However, if the THF solution of ion-sensitive membrane is employed, the thickness of the film may be somewhat thickened.

The film thus produced was then cut out, and constructed as shown in FIG. 11 to produce a chloride ion sensor. The composition of the inner solution 83 used was a 0.2 mol/l KCl solution. The thickness of the ion-sensitive membrane 91 was 220 µm. When the measurement of $Cl^-$ ion concentration on the solutions having $Cl^-$ ion concentration of $10^{-5}$ to $10^{-1}$ mol/l was repeated by using the electrode thus prepared, the repetitive coefficient of variation CV value was found to be within ±1%. Meanwhile, when an ion-sensitive membrane was prepared according to the conventional method by formulating the composition of the ion-sensitive membrane in the same manner as in the case of the above example, the contact angle of the surface which was in contact with the Teflon during the manufacturing step was found to be 60°, which is almost the same as that of the above example, but the contact angle of the surface which was exposed to the outer atmosphere during the manufacturing step was found to be 45°, indicating poor hydrophobic property. The film thus produced was assembled to produce a chloride ion sensor, and the measurement of ion concentration was repeated to find out that the repetitive coefficient of variation CV value thereof was within ±3%. As a result, it was found that the electrode according to this invention is excellent in reproducibility.

Next, another example of the third embodiment will be explained by taking a magnesium ion-selective film as an example.

Figure 14:
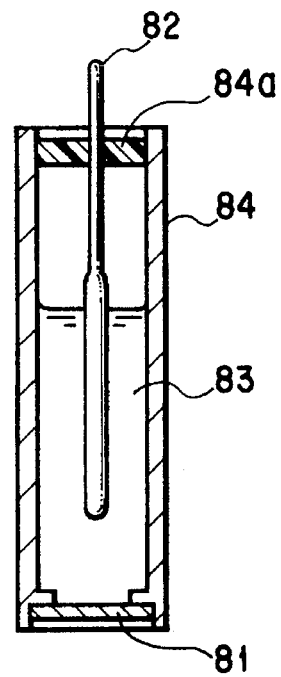
FIG. 14 is a sectional view of a liquid film type ion-selective electrode according to a third embodiment of this invention, in which an internal solution is employed.

A THF solution was prepared by mixing 50 mg of (N', N", N"'-imino-di-8, 1-alkyldiyl)tris(N-heptyl-N-methyl-malonamide) as a sensitive material of a magnesium ion sensor, 45 mg of potassium tetrakis(4-chlorophenyl)borate and 150 mg of tetradodecylammonium tetrakis(4-chlorophenyl)borate as an anion eliminator, and 3.0 g of 2-nitrophenyloctyl ether as a plasticizer. To this THF solution was added polyvinyl chloride in such an amount that the ratio of the polyvinyl chloride becomes 33.0% based on the total of film components excluding THF, thereby preparing a sensitive film solution (THF functioning as a solvent). This film solution was spread onto a Teflon plate in the same manner as the example mentioned above thereby evaporating THF. The atmosphere employed for the evaporation of THF was a dried nitrogen introduced into a globe box (relative humidity: about 5%) in one example, and in another example, the evaporation of THF was carried out in the outer atmosphere in an ordinary manner, in which the relative humidity was about 55%. The contact angle of the film was 63° in the former example, and 42° in the latter example. Then, these films 81 were employed to construct a magnesium ion-selective ion electrode as shown in FIG. 14. In this case, several kinds of film were prepared according to this invention, each being varied in film thickness so as to investigate the film thickness dependency of the selectivity coefficient against calcium ion, which is an important interfering ion for the magnesium ion-selective electrode. In this case, all of the films were prepared from a film solution of the same lot, thereby avoiding the non-uniformity of the mixing ratio of the film-forming components, as well as avoiding any slight difference in manufacturing conditions. The composition of the inner liquid was 0.2 mol/l KCl+0.05 mol/l $MgCl_2$ in every electrodes.

When the measurement of $Mg^{2+}$ ion concentration on the solutions having $Mg^{2+}$ ion concentration of $10^{-5}$ to $10^{-1}$ mol/l was repeated by using the electrodes prepared according to the conventional method and according to this invention, the repetitive coefficient of variation CV value was found to be within ±6% in the case of the conventional method, and within ±3% in the case of this invention, indicating excellency in reproducibility of this invention.

Furthermore, when the electrodes produced according to this invention were investigated on the film thickness dependency of the selectivity coefficient to calcium ion, it was found that when the film thickness was smaller than 30 μm, the selectivity to calcium ion was lowered. However, when the film thickness of the electrode was 30 μm or more, preferably 50 μm or more, the selectivity to calcium ion became almost constant.

As explained above, it is possible according to the third embodiment of this invention to obtain a sensitive film for the ion-selective electrode, which is excellent in fundamental properties desirable for an electrode, such as reproducibility and selectivity.

In addition to the various embodiments as mentioned above, this invention can be modified as follows. Namely, this ion concentration measuring apparatus is provided with n pieces (n≦2) of potentiometric ion sensors, and comprises calibration solution ion concentration-storing means for storing known ion concentrations of plurality of standard solutions, each having different ion concentration; selectivity coefficient-storing means for storing selectivity coefficient of interfering ions of (n−1) kinds in maximum at each ion sensor; calibration curve equation-formulating means for formulating the calibration curve equation of each sensor by measuring the output potential of each sensor in a plurality of standard solutions, and by substituting the values of the output potential thus measured, each known ion concentration and selectivity coefficient stored in the storing means into Nicholsky-Eiseman equation (2); and ion concentration calculating means for determining each ion concentration in a sample solution on the basis of the calibration curve equation of each sensor which has been formulated by the calibration curve equation-formulating means, and on the basis of the output potential of each sensor in the sample solution.

The selectivity coefficient-storing means should be preferably constructed in such a way that it is capable of storing in advance a selectivity coefficient which changes during the immersing time of the sensor, and either a selectivity coefficient which corresponds to the immersing period of the sensors, or a selectivity coefficient which corresponds to the measuring times by the sensors can be employed at the occasion of preparing a calibration curve equation by means of calibration solution ion concentration-storing means.

The ion concentration-storing means may be an ion concentration measuring apparatus comprising ion concentration storing means for storing the ion concentration as determined by calculation; and ion concentration calculation renewing means which takes out the concentration of an interfering ion from the ion concentration storing means and calculates the ion concentration derived from each sensor in a prescribed order, and feeds the latest data of ion concentration to the ion concentration storing means, the measurement of ion concentration from each sensor being repeated at least twice so as to renew the data of ion concentration to obtain the latest ion concentration.

In this manner, the storing of the known ion concentration of plurality of standard solutions having different concentration from each other as well as the selectivity coefficient of an interfering ion can be performed by both of the calibration solution ion concentration-storing means and the selectivity coefficient-storing means.

At this moment, after performing the measurement of output of each sensor in a plurality of standard solutions, the output potential of each sensor, known ion concentration stored in the storing means, and the selectivity coefficient are substituted into the above-mentioned equation (11) by the calibration curve equation formulating means, thereby preparing the calibration curve equation.

In this case, the selectivity coefficient taken out from the selectivity coefficient-storing means is substituted into the equation (11). However, this selectivity coefficient is gradually deteriorated corresponding to the immersing period of time of sensor due to the material of sensor or other factors, and becomes enlarged. Therefore, a selectivity coefficient corresponding to the immersing period of time of sensor is employed for preparing a calibration curve equation.

When the calibration curve equation of each sensor is prepared in this manner, the ion concentration of each sample solution can be determined on the basis of the calibration curve equation prepared as described above and the output potential of each sensor by the ion concentration calculating means.

However, since the value of ion concentration thus obtained through a separate calculation operation by means of the ion concentration calculating means is still accompanied with the influence from the interfering ion in a fairly large extent, the calculation may be repeated by reading out the ion concentration obtained previously from the ion concentration calculating means, thereby making it possible to obtain more accurate measurement of ion concentration in the sample solution.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An ion concentration measuring apparatus for measuring the concentration of a measuring ion in a sample solution containing the measuring ions and an interfering ion having the same ionic charge number as that of the measuring ion, which comprises:

a first ion-selective electrode for generating an output potential in response to the measuring ion;

a second ion-selective electrode for generating an output potential in response to the interfering ion;

means for sequentially contacting the first and second ion-selective electrodes with a first standard solution, a second standard solution and a third standard solution, each containing known concentrations of the measuring ions and the interfering ions, a concentration of the measuring ion contained in the first standard solution being substantially distinct from a concentration of the measuring ion contained in the second standard solution, and a concentration of the interfering ion contained in the first standard solution being substantially distinct from a concentration of the interfering ion contained in the second standard solution;

a first arithmetic means for calculating factors of calibration curves of the first and second ion-selective electrodes on the basis of the output potential of the first and second ion-selective electrodes, which have been obtained through the contact thereof with the first, second and third standard solutions;

means for contacting the sample solution with the first and second ion-selective electrodes;

a second arithmetic means for calculating the concentration of the measuring ion in the sample solution on the basis of the output potentials of the first and second ion-selective electrodes which has been obtained through the contact thereof with the sample solution and the calibration curves which has been obtained from the first arithmetic means; and a ratio between the concentration of the measuring ion and the interfering ion in the first standard solution being identical to a ratio between the concentrations of the measuring ion and the interfering ion in the second standard solution, and not identical to a ratio between the concentrations of the measuring ion and the interfering ion in the third standard solution.

2. The ion concentration measuring apparatus according to claim 1, wherein the concentration of the measuring ion in the third standard solution is lower than the concentration of the interfering ion.

3. The ion concentration measuring apparatus according to claim 1, wherein the first arithmetic means is adapted to calculate $E°$, $\alpha$ and $K_{MN}$ in the following equation, and the second arithmetic means is adapted to calculate a concentration of the measuring ion in the sample solution on the basis of the output potential of the first ion-selective electrode, which has been obtained upon contact thereof with the sample solution, and of the output potential of said second ion-selective electrode, which has been obtained upon contact thereof with the sample solution:

$$E = E° + \alpha \log[a_M + \Sigma K_{MN}(a_N)]$$

where $E°$ is an output potential in a standard state, $\alpha$ is the slope, $a_M$ is the activity of measuring ions, $K_{MN}$ is a selectivity coefficient to an interfering ion, $a_N$ is the activity of an interfering ion.

4. The ion concentration measuring apparatus according to claim 3, wherein the first arithmetic means is adapted to calculate $E°$, $\alpha$ and $K_{MN}$, and to formulate a calibration curve according to the equation by using the values of $E°$, $\alpha$ and $K_{MN}$ thus calculated.

5. The ion concentration measuring apparatus according to claim 1, which further comprises a reference electrode, a first potential difference measuring circuit for measuring a potential difference between the reference electrode and the ion-selective electrode, and a second potential difference measuring circuit for measuring a potential difference between the reference electrode and another ion-selective electrode, and wherein said first and second arithmetic means constitute a calculated result storing element connected to the first and second potential difference measuring circuits, and the calculation storing element is adapted to store the known concentrations of the first, second and third standard solutions.

6. The ion concentration measuring apparatus according to claim 1, which further comprises means for passing the first, second, third standard solutions and the sample solution; a change-over means for change over the flows of the first, second, third standard solutions and the sample solution; and means for sequentially contacting the first, second, third standard solutions and the sample solution to the ion-selective electrode and to said another ion-selective electrode.

7. The ion concentration measuring apparatus according to claim 1, wherein the measuring ions are magnesium ions, and the interfering ions are calcium ions.

8. The ion concentration measuring apparatus according to claim 1, wherein the measuring ions are ammonium ions, and the interfering ions are potassium ions.

9. A method for measuring a concentration of measuring ions in a sample solution containing the measuring ion and an interfering ion having the same ionic charge number as that of the measuring ion, which comprises:

a step of contacting first and second ion-selective electrodes for generating an output potential in response to the measuring ion sequentially with a first standard solution, a second standard solution and a third standard solution, each containing known concentrations of the measuring ion and the interfering ion, a concentration of the measuring ion contained in the first standard solution being substantially distinct from a concentration of the measuring ion contained in the second standard solution, and a concentration of the interfering ion contained in the first standard solution being substantially distinct from a concentration of the interfering ion contained in the second standard solution;

a first calculating step of calculating factors of calibration curves of the first and second ion-selective electrodes on the basis of the output potential of the first and second ion-selective electrodes, which have been obtained through the contact thereof with the first, second and third standard solutions;

a step of contacting the sample solution with the first ion-selective electrode;

a step of contacting the sample solution with a second ion-selective electrode for generating an output potential in response to the interfering ion;

a second calculating step for calculating the concentration of the measuring ion in the sample solution on the basis of the output potentials of the first and second ion-selective electrodes which have been obtained through the contact thereof with the sample solution and the calibration curves which have been obtained from the first calculating step; and a ratio between the concentrations of the measuring ion and the interfering ion in the first standard solution being identical to a ratio between the concentrations of the measuring ion and the interfering ion in the second standard solution, and not identical to a ratio between the concentrations of the measuring ion and the interfering ion in the third standard solution.

10. The method for measuring a concentration of an measuring ion according to claim 9, wherein the concentration of the measuring ion in the third standard solution is lower than the concentration of the interfering ion.

11. The method for measuring a concentration of an measuring ion according to claim 9, wherein the first calculating step is carried out to calculate $E°$, $\alpha$ and $K_{MN}$ in the following equation, and the second calculating step is carried out to calculate a concentration of the measuring ion in the sample solution on the basis of the output potential of the first ion-selective electrode, which has been obtained upon contact thereof with the sample solution, and of the output potential of the second ion-selective electrode, which has been obtained upon contact thereof with the sample solution:

$$E = E° + \alpha \log[a_M + \Sigma K_{MN}(a_N)]$$

where $E°$ is an output potential in a standard, $\alpha$ is slope $a_M$ is the activity of an measuring ion, $K_{MN}$ is a selectivity coefficient to an interfering ion, $a_N$ is the activity of an interfering ion.

12. The method for measuring a concentration of an measuring ion according to claim 11, wherein the first calculating step is carried out to calculate $E°$, $\alpha$ and $K_{MN}$, and to formulate a calibration curve according to the equation by using the values of $E°$, $\alpha$ and $K_{MN}$ thus calculated.

13. The method for measuring a concentration of an measuring ion according to claim 9, which further comprises a step of passing the first, second, third standard solutions and the sample solution; a step of changing over the flows of the first, second, third standard solutions and the sample solution; and a step of sequentially contacting the first, second, third standard solutions and the sample solution to the first ion-selective electrode and to the second ion-selective electrode.

14. The method for measuring a concentration of an measuring ion according to claim 9, wherein the measuring ion is magnesium ion, and the interfering ion is calcium ion.

15. The method for measuring a concentration of an measuring ion according to claim 9, wherein the measuring ion is ammonium ion, and the interfering ion is potassium ion.

16. A flow-cell type ion concentration measuring apparatus for measuring the concentrations of magnesium ion and calcium ion in a sample solution, which comprises:

a flow-cell channel for passing the sample solution containing magnesium ion and calcium ion therethrough;

a polyvinyl chloride liquid film magnesium ion-selective electrode disposed in the flow-cell channel for detecting the concentration of magnesium ion; and a calcium ion-selective electrode containing a film solvent selected from the group consisting of decan-1-ol, di-n-octylphenyl phosphonate, dioctylphosphonate, tri-n-octylphosphate and tri-n-decylphosphate and disposed at the downstream of the magnesium ion-selective electrode in the flow-cell channel for detecting the concentration of calcium ion.

17. The flow-cell type ion concentration measuring apparatus according to claim 16, which further comprises a reference electrode disposed at a portion within the flow-cell channel.

18. An ion concentration measuring apparatus for measuring the concentration of a measuring ion in a sample solution containing the measuring ions and an interfering ion having the same ionic charge number as that of the measuring ion, which comprises:

an ion-selective electrode for generating an output potential in response to the measuring ion;

means for sequentially contacting the ion-selective electrode with a first standard solution, a second standard solution and a third standard solution, each containing known concentrations of the measuring ions and the interfering ions, a concentration of the measuring ion contained in the first standard solution being substantially distinct from a concentration of the measuring ion contained in the second standard solution, and a concentration of the interfering ion contained in the first standard solution being substantially distinct from a concentration of the interfering ion contained in the second standard solution;

an arithmetic means for calculating a selectivity coefficient of the ion-selective electrode on the basis of the output potential of the ion-selective electrode, which has been obtained through the contact thereof with the first, second and third standard solutions; and second ion-selective electrodes;

a ratio between the concentration of the measuring ion and the interfering ion in the first standard solution being identical to a ratio between the concentration of the measuring ion and the interfering ion in the second standard solution, and not identical to a ratio between the concentrations of the measuring ion and the interfering ion in the third standard solution.

19. A method for measuring a concentration of measuring ion in a sample solution containing the measuring ion and an interfering ion having the same ionic charge number as that of the measuring ion, which comprises:

a step of contacting an ion-selective electrode for generating an output potential in response to the measuring ion sequentially with a first standard solution, a second standard solution and a third standard solution, each containing known concentrations of the measuring ion and the interfering ion, a concentration of the measuring ion contained in the first standard solution being substantially distinct from a concentration of the measuring ion contained in the second standard solution, and a concentration of the interfering ion contained in the first standard solution being substantially distinct from a concentration of the interfering ion contained in the second standard solution;

a calculating step of calculating a selectivity coefficient of the ion-selective electrode on the basis of the output potential of the ion-selective electrode, which have been obtained through the contact thereof with the first, second and third standard solutions;

a step of contacting the sample solution with the ion-selective electrode; and a ratio between the concentrations of the measuring ion and the interfering ion in the first standard solution being identical to a ratio between the concentrations of the measuring ion and the interfering ion in the second standard solution, and not identical to a ratio between the concentrations of the measuring ion and the interfering ion in the third standard solution.

* * * * *